United States Patent
Su et al.

[11] Patent Number: 6,130,323
[45] Date of Patent: Oct. 10, 2000

[54] NON-NUCLEOTIDE LINKING REAGENTS

[75] Inventors: Sheng-Hui Su, San Ramon; Rajkumar Siva Iyer, Dublin; Sunil K. Aggarwal, Pleasanton; Krishan L. Kalra, Danville, all of Calif.

[73] Assignee: BioGenex Laboratories, San Ramon, Calif.

[21] Appl. No.: 09/171,925
[22] PCT Filed: May 15, 1997
[86] PCT No.: PCT/US97/09094
 § 371 Date: Oct. 26, 1998
 § 102(e) Date: Oct. 26, 1998
[87] PCT Pub. No.: WO97/43451
 PCT Pub. Date: Nov. 20, 1997

Related U.S. Application Data

[63] Continuation of application No. 08/647,820, May 15, 1996, abandoned.

[51] Int. Cl.[7] .......................... C07H 19/00; C07H 21/00; C07H 21/02; C07H 21/04
[52] U.S. Cl. ...................... 536/23.1; 536/22.1; 536/25.3; 536/25.31; 536/25.32
[58] Field of Search ................... 536/22.1, 23.1, 536/25.3, 25.31, 25.32

Primary Examiner—Jezia Riley
Attorney, Agent, or Firm—James C. Weseman, Esq.; The Law Offices of James C. Weseman

[57] ABSTRACT

Non-nucleotide reagents capable of forming oligomers with nucleotide units are disclosed, together with intermediates for synthesizing such non-nucleotide reagents, oligomers incorporating such reagents, kits containing such reagents and methods for their use in forming oligomers with nucleotide units.

20 Claims, 5 Drawing Sheets

Scheme 1a:

Scheme 1a:

Scheme 3: Synthesis of compound 3

NON-NUCLEOTIDE LINKING REAGENTS

This application is a 371 of PCT/US 97/09094 filed May 15, 1997 and continuation of Ser. No. 08/647,820 filed May 15, 1996, now abandoned.

TECHNICAL FIELD

The present invention relates generally to the use of non-nucleotide reagents as monomeric units in oligonucleotides.

BACKGROUND OF THE INVENTION

In both research applications and clinical diagnosis, a known technique for determining the presence of a particular nucleotide sequence (the "target nucleotide sequence") in either RNA or DNA is to perform a nucleic acid hybridization assay. In such an assay, a nucleotide probe, typically an oligonucleotide, is selected having a nucleotide sequence complementary to at least a portion of the target nucleotide sequence. Typically, the probe is labeled to provide a means whereby the presence of the probe can be readily detected.

When the labeled probe is exposed to a sample suspected of containing the target nucleotide sequence, under hybridizing conditions, the target sequence will hybridize with such a labeled probe. The presence of the target sequence in the sample can then be determined qualitatively or quantitatively, usually after separating hybridized and non-hybridized probes and determining the presence or amount of the labeled probe which hybridized to the test sample.

Prior methods for linking a label to a nucleotide probe have generally utilized a single label attached to a nucleotide monomeric unit, and then incorporating one or more of the nucleotide monomeric units into the probe. For example, analogs of dUTP and UTP containing a biotin moiety have been chemically synthesized and incorporated into polynucleotides (P. R. Langer et al., *Proc. Nat. Acad. Sci. USA* 78:6633 (1981)). Such biotin-labeled nucleotides may then be incorporated into nucleic acid probes of biological or synthetic origin.

Other methods for labeling nucleotide probes have been proposed which allow labels to be randomly linked to nucleotides in a nucleotide multimer. Numerous proposals have been made for incorporating multiple modified nucleotides or non-nucleotide monomeric units into oligonucleotides with a view towards enhancing the detectability of the labeled probe and the target nucleotide sequence.

However, it has been demonstrated that use of such labeled nucleotides in a probe can reduce the stability of the hybrid formed with a target nucleotide sequence, particularly when multiple labels are present. Such reduced hybrid stability has been demonstrated for nucleic acid probes of biological origin possessing multiple biotin moieties, for synthetic oligonucleotides possessing multiple fluorescein labels, as well as for synthetic oligonucleotides possessing biotin and fluorescein labels.

In addition, derivatives of nucleotide linking phosphate groups have been disclosed, the nucleophilic moiety of which can be labeled following their incorporation into an oligonucleotide. However, such compounds, being based on nucleotide derivatives, would be expected to exhibit some of the disadvantages discussed above for nucleotide based derivatives.

More recently, 2-amino-1,3-propanediol structures have been used to label oligonucleotides with reporter groups (Nelsen, P. S. et al., *Nuc. Acids Res.* 20:6253 (1992)). However, these structures appear to demonstrate low coupling efficiency, and thus low yield of labeled oligonucleotides which furthermore must be carefully purified before they can find use as probes for target sequences.

Thus it is considered desirable to provide a non-nucleotide reagent which demonstrates high coupling efficiency and thus provides higher yield of labeled oligomer.

Furthermore, it is also considered desirable to provide such a reagent which will allow the resultant oligomers to anneal and hybridize with efficiencies approaching those of oligomers which contain only native nucleotide monomeric units.

DISCLOSURE OF THE INVENTION

The present invention provides non-nucleotide reagents capable of forming an oligomer with nucleotide units, said reagents comprising compounds of the formula:

$$R^1-X-CH_2-C(=X^1)(-X^2-X^3)-CH_2-R^3$$

wherein $R^1$ is selected from the group consisting of hydrogen, acid-sensitive, base-stable blocking groups and acyl capping groups;

X is selected from the group consisting of O, S, NH and N=N;

$X^1$ is a substituted or unsubstituted $C_5$ to $C_7$ cyclic moiety incorporating the carbon atom of the formula;

$X^2$ is selected from the group consisting of O, S, $CH_2$, NH and N=N; and $X^3$ is hydrogen or a linking functional group which is capable of linking with a functional moiety; and $R^3$ is a linking group of the formula $$-OP(X^4)(X^5) \quad \text{or} \quad -OP(=O)(X^6)(X^7)$$
$$\text{(a)} \qquad\qquad \text{(b)}$$

wherein $X^4$ is halogen or substituted amino, $X^5$ is alkyl, alkoxy or phenoxy, or a cyano derivative thereof, $X^6$ is halogen, amino or O, and $X^7$ is alkyl, alkoxy or aryloxy, or may be H only if $X^6$ is O, or $R^3$ is a bond, either directly or through an intermediate group, to a solid support. Such reagents can be used to label or otherwise incorporate desirable functionalities into oligomers, utilizing conventional automated nucleotide synthetic protocols. The present reagents preserve the natural three carbon internucleotide phosphate distance, so as to preserve the hybridization and annealing properties of the nucleotide duplex.

Also provided in the present invention are intermediates useful for producing such non-nucleotide reagents, oligomers incorporating such reagents, kits containing such reagents and methods for use of the reagents in forming oligomers with nucleotide units.

DETAILED DESCRIPTION OF THE INVENTION

Figure 1:
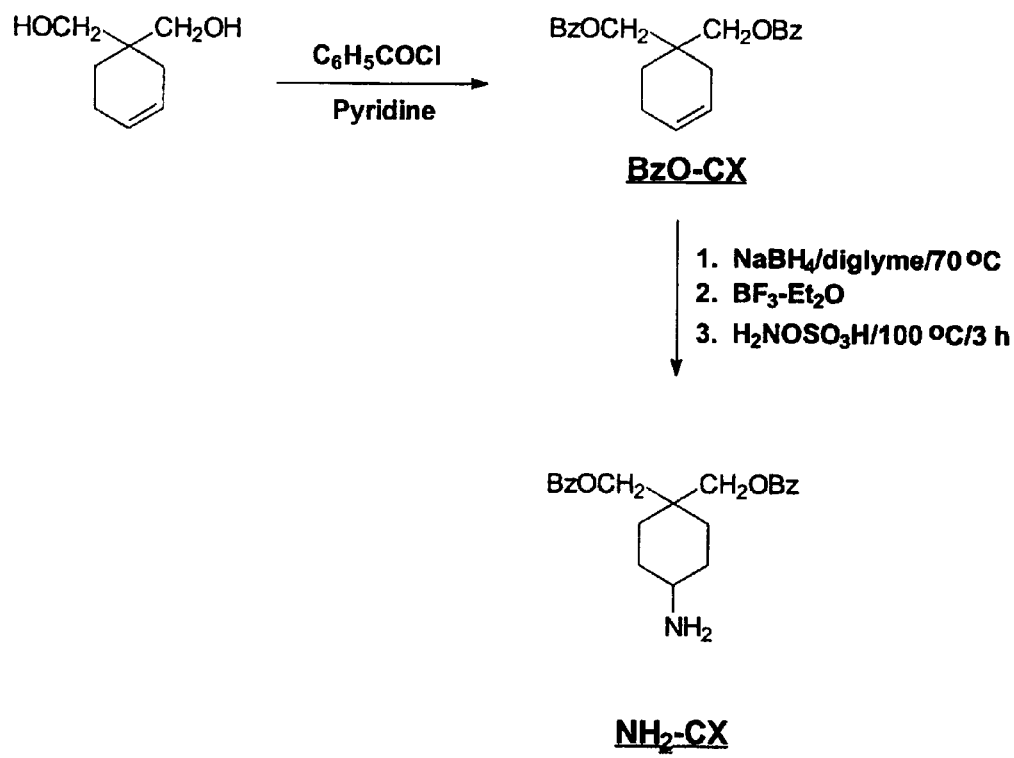
FIG. 1 is a schematic depiction of the synthetic protocol of Example 1(a), steps I and II.

The present invention provides non-nucleotide reagents capable of forming an oligomer with nucleotide units, said reagents comprising compounds of the formula:

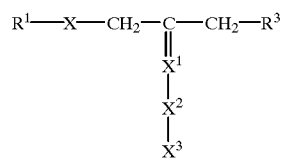

wherein $R^1$ is selected from the group consisting of hydrogen, acid-sensitive, base-stable blocking groups and acyl capping groups;

X is selected from the group consisting of O, S, NH and N=N;

$X^1$ is a substituted or unsubstituted $C_5$ to $C_7$ cyclic moiety incorporating the carbon atom of the formula;

$X^2$ is selected from the group consisting of O, S, $CH_2$, NH and N=N; and $X^3$ is hydrogen, or a linking functional group which is capable of linking with a functional moiety; and $R^3$ is a linking group of the formula

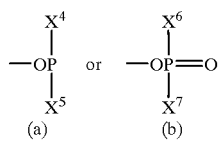

wherein $X^4$ is halogen or substituted amino, $X^5$ is alkyl, alkoxy or phenoxy, or a cyano derivative thereof, $X^6$ is halogen, amino or O, and $X^7$ is alky, alkoxy or aryloxy, or may be H only if $X^6$ is O, or $R^3$ is a bond, either directly or through an intermediate group, to a solid support.

In the disclosure which follows, the following terms will have the indicated meanings unless a contrary meaning is otherwise apparent from the context in which the term is used.

As used herein, the term "nucleotide" is taken to mean a subunit of a nucleic acid consisting of a phosphate group, a five carbon sugar and a nitrogen-containing base. The term is also taken to include analogs of such subunits.

As used herein, the term "nucleotide oligomer" or "oligomer" is taken to mean a chain of nucleotides linked by phosphodiester bonds or analogs thereof.

As used herein, the term "nucleotide oligomer containing non-nucleotide monomers" is taken to mean an oligomer comprised of nucleotide units together with non-nucleotide monomeric units linked by phosphodiester bonds or analogs thereof.

The present invention provides a non-nucleotide reagent which can be coupled synthetically with nucleotide monomeric units to produce a defined sequence oligomer with a backbone comprised of nucleotide and non-nucleotide monomeric units.

In the formula first provided above,

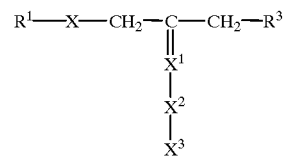

$R^1$ is a substituent group which is intended to be removed to facilitate linkage with other units in the backbone structure of a nucleotide oligomer containing non-nucleotide monomers. As such, $R^1$ is generally selected from the group consisting of hydrogen, acid-sensitive, base-stable blocking groups and acyl capping groups. Such groups are well known in the art, and include, for example, triphenylmethyl compounds, and alkoxy derivatives thereof, such as dimethoxytriphenyl (DMT) groups.

The group identified as X functions in part to maintain proper intramolecular distance in the non-nucleotide reagent when functioning as a monomeric unit. Typically, X is selected from the group consisting of O, S, NH and N=N, although other atoms, or groups of atoms, could also serve in this capacity. Most commonly, X will be O.

The groups identified as $X^1$, $X^2$, and $X^3$ are substituent groups which are intended to facilitate linkage with other functional moieties, and other functional groups, which may be desired to be included in a nucleotide oligomer containing non-nucleotide monomers.

Due to the chemical nature of the present non-nucleotide reagent, it may be positioned at any desired point within the nucleotide oligomer sequence. Thus it is possible to design a wide variety of properties into oligomers which contain both nucleotide and non-nucleotide monomeric units. Such properties include the attachment of specific moieties herein termed "functional moieties" at any desired location within the oligomer. Such moieties can include (but are not limited to) detectable labels (including enzymatic, fluorogenic, radioactive, chemiluminescent, and the like), intercalating agents, metal chelators, drugs, hormones, proteins, peptides, radical generators, nucleolytic agents, proteolytic agents, catalysts, specific binding agents (including biotin, antigens, haptens, antibodies, receptors, and the like), and other substances of biological interests, together with agents which modify DNA transport across a biological barrier, (such as a membrane), and substances which alter the solubility of a nucleotide multimer. Thus it is possible to position such labels and agents adjacent to any desired nucleotide.

The groups $X^1$, $X^2$, and $X^3$ will comprise a substituent to the carbon backbone of the formula in which: $X^1$ is a substituted or unsubstituted $C_5$ to $C_7$ cyclic moiety incorporating the carbon atom of the formula; $X^2$ is selected from the group consisting of O, S, $CH_2$, NH and N=N; and $X^3$ is a linking functional group which is capable of linking with a functional moiety. In the present reagent, the rigidity of the chemical structure of $X^1$ provides that desirable feature of extending the linkage group and functional moiety away from the oligomeric backbone structure, thereby substantially enhancing the coupling efficiency of the reagents of the present invention. Commonly, $X^1$ will be substituted or unsubstituted cyclohexane.

The group identified as $X^2$ functions as a linking and modifiable reactive group. Typically, $X^2$ is selected from the group consisting of O, S, NH, $CH_2$, and N=N, although other atoms, or groups of atoms, could also serve in this capacity. Most commonly, $X^2$ will be NH.

In the formula, $X^3$ is hydrogen, or a linking functional group which can be of any length appropriate to the particular functional moiety selected. Typically, $X^3$ is a group of the formula

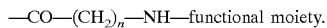

—CO—$(CH_2)_n$—NH—functional moiety.

wherein n is an integer from 0 to 20. It is of course within the invention to add the functional moiety to the reagent prior to, or after, the inclusion of the reagent as a monomeric unit in an oligomer. In addition, the functional moiety can also serve as a bond to a solid support.

In the formula, $R^3$ is a substituent group which is intended to facilitate linkage with other units in the backbone structure of a nucleotide oligomer containing non-nucleotide monomers or to solid supports and the like. Typically, such linkage will be accomplished by automated methodologies, such as automated DNA/RNA synthetic protocols. As such, $R^3$ is generally selected from the group consisting of phosphodiesters, phosphotriesters, phosphites, phosphoramidites, H-phosphonates, alkyl-phosphonates, and phosphorothioates. Such groups are well known in the art, and include, for example, phosphorus linking group of the formula

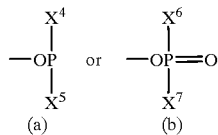

wherein $X^4$ is halogen or substituted amino, $X^5$ is alkyl, alkoxy or phenoxy, or a cyano derivative thereof, $X^6$ is halogen, amino or O, and $X^7$ is alkyl, alkoxy or aryloxy, or may be H only if $X^6$ is O, or $R^3$ is a bond, either directly or through an intermediate group, to a solid support.

As discussed above, the present non-nucleotide reagents will possess a linker functionality to which desired chemical moieties have been or can be attached, either prior to or after initiating the synthesis of the nucleotide oligomer.

In general, the techniques for linking moieties to the linker arm will be similar to the techniques known for linking labels to groups on proteins. Examples of useful chemistries include a reaction of alkyl amines with active esters, active imines, aryl fluorides or isothiocyanates, and the reaction of thiols with maleimides, haloacetyls, etc. (see generally Means, G. M. and R. E. Feeney, "Chemical Modification of Proteins" Holden-Day Inc. (1971); R. E. Feeney, *Int. J. Peptide Protein Res.* 29:145–161 (1987)).

As discussed above, due to the chemical nature of the present non-nucleotide reagent, it may be positioned at any desired point within the nucleotide oligomer sequence. Thus it is possible to design a wide variety of properties into oligomers which contain both nucleotide and non-nucleotide monomeric units. Such properties include the attachment of specific functional moieties at any desired location within the oligomer.

Other benefits provided by the practice of the present invention include the ability to immobilize the defined sequence to a solid support by employing the linker arm functionality conjoined to a chemical moiety of the support in order to construct, for example, nucleotide affinity supports. Multiple chemical moieties can also be incorporated into the oligomer through multiple non-nucleotide monomeric units in a particular nucleotide oligomeric sequence.

One can also provide oligomers which differ from naturally occurring polynucleotides in that they include altered activities by utilizing proteins and enzymes which act on polynucleotides. For example, the placement of the non-nucleotide monomeric unit on the 3' terminus of an otherwise pure polynucleotide will impart resistance to degradation by snake venom phosphodiesterases, or providing specific cleavage sites for selected nucleases.

Hybridization probes may also be constructed by interspersing hybridizable nucleotide monomeric units and non-nucleotide monomeric units. For example, a mixed synthesis of nucleotide and non-nucleotide monomers can be performed whereby a defined sequence of nucleotide monomers are synthesized followed by a sequence of one or more non-nucleotide monomeric units, optionally followed by a second block of a defined sequence of nucleotide monomers.

The present invention also provides the ability to construct synthetic probes which simultaneously detect nucleotide multimers which differ by one or more base pairs. This can be accomplished by using the non-nucleotide reagents described herein to replace the nucleotides in a probe with non-nucleotide monomeric units at selected sites where differences occur in the nucleotide sequence of the various target nucleotide sequences.

In selected embodiments of the invention, labeled hybridization probes are constructed as oligomers with a defined sequence comprised of nucleotide and non-nucleotide monomers. Such non-nucleotide monomeric units can be grouped in a selected region or interspersed throughout the sequence of the nucleotide oligomer. The non-nucleotide monomeric units can be chemically labeled for use in hybridization reactions.

In the present invention, the non-nucleotide reagent is provided in a manner which permits it to be added in a stepwise fashion to produce a mixed nucleotide, non-nucleotide oligomer employing current DNA/RNA synthesis methods. Such reagents would normally be added in a stepwise manner to attach the corresponding monomeric unit to an increasing oligonucleotide chain which is covalently immobilized to a solid support. Typically, the first nucleotide is attached to the support through a cleavable ester linkage prior to the initiation of synthesis. In the present invention, the non-nucleotide reagent can be provided conveniently linked to such solid supports, for example, to controlled pore glass (CPG), to resins, polymers such as polystyrene, and the like. Stepwise extension of the oligonucleotide chain is normally carried out in the 3' to 5' direction. Such nucleic acid synthesis methods are provided, for example, in S. A. Narang, "Synthesis and Applications of DNA and RNA," Academic Press (1987) and in M. J. Gait "Oligonucleotide Synthesis," IRL Press, Washington, D.C. (1984).

When synthesis is complete, the oligomer is cleaved from the support by hydrolyzing the ester linkage and the nucleotide originally attached to the support becomes the 3' terminus of the resulting oligomer. Accordingly, the present invention provides both a reagent for preparing oligomers which contain a mixture of nucleotide and non-nucleotide monomeric units, together with methods for utilizing such reagents in the construction of such oligomers, Typically, the present reagents will possess two coupling groups so as to permit the stepwise inclusion into a oligomer of nucleotide and non-nucleotide monomeric units. The first of said coupling groups will have the property that it can couple efficiently to the terminus of a growing chain of monomeric units. The second of said coupling groups is capable of further extending, in a stepwise fashion, the growing chain of mixed nucleotide and non-nucleotide monomers. This typically requires that the second coupling group be inactivated while the first coupling group is coupled, so as not to substantially couple at that time, the second coupling group can thereafter be activated so as to then couple the non-nucleotide monomeric unit. The inactivation is preferably accomplished with a protecting group on the second coupling group, which can then be removed to activate the second coupling group. It is also considered to be within the scope of the invention that such "inactivation" and "activation" might be accomplished simply by changing reaction conditions (e.g. pH, temperature, concentration of reagents, and the like) with second coupling groups of suitable chemical structure which also lend themselves to inactivation and activation by such techniques. Such coupling groups permit the adjacent attachment of either nucleotide or non-nucleotide monomeric units. It is considered desirable that such coupling groups operate through coupling and deprotection steps which are compatible with standard automated DNA synthesis methods.

Such methods typically require that synthesis occur unidirectionally and that all coupling cleavage and deprotection steps occur under "nonadverse conditions" that is they do not substantially adversely effect the oligomer backbone and its various components.

Thus, the present invention provides oligomers containing the present non-nucleotide reagents, as well as methods for using such reagents in the synthesis of oligomers containing both nucleotide and non-nucleotide units.

The invention further provides intermediates which are useful to synthesize the present non-nucleotide reagents. One embodiment of such an intermediate is provided by the formula:

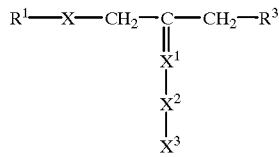

wherein
$R^1$ is hydrogen; X is oxygen;
$X^1$ taken together with the carbon atom of the formula is cyclohexane, $X^2$ is NH, and $X^3$ is H; and
$R^3$ is OH.
In this embodiment, the intermediate is of a structure similar to that of the present reagents, without having the functional groups included at $R^1$, $X^3$ and $R^3$.

In order to facilitate the use of the present reagents, kits for use in constructing oligomer can be provided to simplify practice of the method described above. The kit will typically contain a receptacle adapted to hold one or more individual reagent containers and at least a first container containing (1) a reagent in accordance with the formula

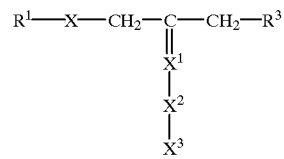

wherein $R^1$, X, $X^1$, $X^2$, $X^3$, and $R^3$ are as previously defined. The reagent can be provided as a solution comprising a solvent and the reagent or (2) the reagent in an amount appropriate to make up the desired concentration when solvent from another container is used to fill the reagent container to a predetermined level.

In many cases, the kit will also contain at least a second container containing (1) a reagent used in the synthesis of oligomers, or (2) a reagent used in the detection of the functional moiety included in the subject reagent, or containers with both such materials. Such reagents are well known in the art and require no further description here. Specific examples are given in the general examples of the invention set out below. Appropriate instructions for carrying out the method of the invention will also be included in the kit.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms (μg), nanograms (ng), or picograms (pg), all amounts are given in moles (mol), millimoles (mmol), micromoles (μmol), nanomoles (nmol), picomoles (pmol), or femtomoles (fmol), all concentrations are given as percent by volume (%), proportion by volume (v:v), molar (M), millimolar (mM), micromolar (μM), nanomolar (nM), picomolar (pM), or normal (N), all volumes are given in liters (L), milliliters (mL), or microliters (μL), and linear measurements are given in millimeters (mm), or nanometers (nm) unless otherwise indicated.

The following examples serve to demonstrate the synthesis of reagents of the present invention, as well as their use in forming oligomers with nucleotide units in accordance with the invention.

In the examples, the following abbreviations are used: "CX" is intended to refer to cyclohexane, "Bz" is intended to refer to benzoyl, "CED" is intended to refer to cyanoethyl N,N-diisopropyl phosphoramidite and "LC" is intended to refer to long chain.

EXAMPLE 1

Reagents in accordance with the present invention can be synthesized in accordance with chemical synthetic techniques well known in the art. The following synthetic protocols demonstrate the synthesis of selected compound within the scope of the present invention.

(a) Synthesis of Reagent compound 1 wherein $R^1$ is dimethoxytriphenyl (DMT), X is O, $X^1$—$X^2$—$X^3$ is cyclohexane —NH—CO—biotin, and $R^3$ is phosphoramidite.

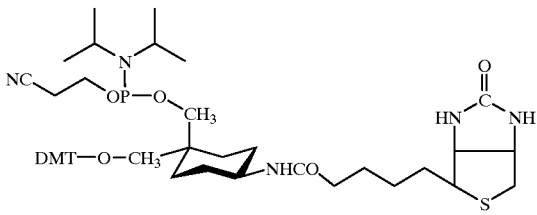

[COMPOUND 1]

Figure 2:
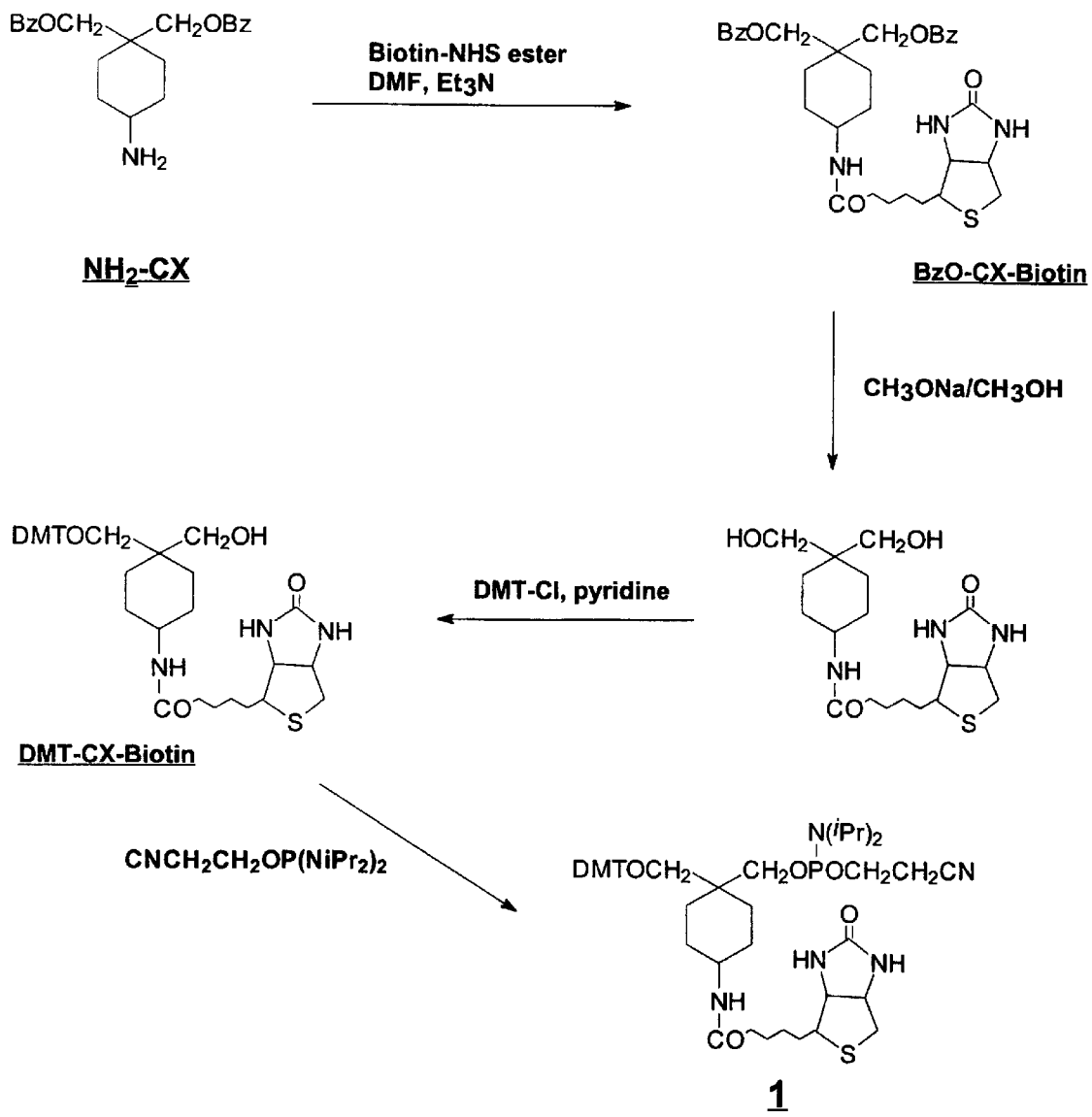
FIG. 2 is a schematic depiction of the synthetic protocol of Example 1(a), steps III, IV and V.

The synthetic protocol for Compound 1 is outlined below and depicted in FIGS. 1 and 2:

Step I: Synthesis of BzO-CX

To an ice-cold solution of 500 g 4,4-bis(hydroxymethyl)-1-cyclohexene in 3.0 L of pyridine, was added dropwise 1.03 L of benzoyl chloride. The reaction mixture was stirred at room temperature overnight, when TLC analysis (ethyl acetate/hexane 1:4 v/v) indicated the reaction to be complete. The reaction was quenched by the addition of 100 mL water, followed by stirring at room temperature for 1 hour.

The reaction mixture was evaporated in vacuo to afford a syrupy residue. This was dissolved in methylene chloride and washed with 5% aqueous $NaHCO_3$ solution. The organic solution was dried over anhydrous sodium sulfate, filtered, and concentrated in vacuo to afford 1,500 g of crude product.

This product was purified by column chromatography over silica gel, using ethyl acetate/hexane (1:4, v/v) to elute the product (yield 1,050 g). The desired product was dried under high vacuum for 2 days.

Step II: Synthesis of $NH_2$-CX

To a stirred solution of 120 g of BzO-CX in 300 mL diglyme, under argon, was added dropwise a solution of 5.5 g $NaBH_4$ in 150 mL of diglyme. The reaction mixture was slowly heated to 70° C. A solution of 23.4 mL of $BF_3$-$Et_2O$ in 30 mL diglyme was then slowly added to the reaction mixture and the resulting mixture stirred at 70° C. for 1 hour. The reaction was quenched by the addition of 2.5 mL water. This was followed by the addition of 50 g of hydroxylamine-O-sulfonic acid and the reaction mixture was heated at 100° C. for 3 hours. The reaction mixture was cooled to room temperature and then extracted into 1.2 L of methylene chloride. The organic extract was washed with 500 mL water, followed by 5% $NaHCO_3$ solution (2×300 mL). The organic layer was dried over anhydrous sodium sulfate, filtered, and solvents removed by rotary evaporation to give 270 g of crude product.

Purification of the product by silica gel column chromatography, using a solvent system comprising of 2.5–8.0% methanol in methylene chloride to elute the product, afforded 50 g of pure 4-amino isomer of $NH_2$-CX. Small quantities of the undesired 3-amino isomer of $NH_2$-CX were also formed.

Step III: Synthesis of BzO-CX-Biotin

To 13.5 g of the amino compound $NH_2$-CX obtained above, was added 200 mL of methylene chloride. To the resulting solution was added 18.8 g of Biotinyl N-hydroxysuccinimide ester (Biotin-NHSu) dissolved in 200 mL of DMF. The reaction mixture was stirred for 15 min at room temperature, followed by the addition of 10.3 mL triethylamine. The reaction was allowed to proceed for 1.5 hours, when TLC analysis revealed the reaction to be complete.

Methylene chloride was removed by rotary evaporation, and the resulting residue treated with 30 mL methanol and with 25 mL of 10% aqueous sodium carbonate solution. The solution was stirred at room temperature for 1 hour and then extracted with 1.2 L of ethyl acetate. The organic layer was washed with brine (2×400 mL), dried over anhydrous sodium sulfate, filtered, and solvents removed in vacuo to finally give 22 g of crude product.

This product was purified by column chromatography over silica gel, using gradient elution with 2.5–8.0% methanol in methylene chloride to yield 15 g.

Step IV: Synthesis of DMT-CX-Biotin

To a stirred solution of 14.3 g of BzO-CX-Biotin in 200 mL DMF, was added 20 mL of 25% sodium methoxide in methanol, and the resulting mixture stirred at 0–5° C. for 1 hour. The pH of the solution was then adjusted to 7.0 by the addition of 60 g Dowex 50X8-100 resin to the reaction mixture followed by stirring for 15 min. The resin was filtered off and the filtrate evaporated to remove DMF. The resulting residue was dissolved in 10 mL methylene chloride and the product precipitated by the addition of 100 mL hexane. The product was then dried under high vacuum.

The crude product obtained in this manner was azeotroped twice with pyridine and then dissolved in 300 mL pyridine. To this was added 8.13 g of DMT-Cl and the reaction mixture stirred at room temperature, under argon, for 1.5 hours. The reaction was quenched by the addition of 5 mL methanol. The reaction mixture was taken up in 1 L methylene chloride, the organic extract washed with 5% $NaHCO_3$ solution, and then dried over anhydrous sodium sulfate. Evaporation of the solvents in vacuo afforded 26 g of crude product, which was purified by column chromatography over silica gel, eluting with methylene chloride/methanol (100:4 v/v) to yield 5.7 g.

Step V: Synthesis of Biotin-CX-CED Phosphoramidite

The intermediate obtained in step IV above was converted to the corresponding phosphoramidite using standard methods. Thus, 4.0 g of DMT-CX-Biotin was dissolved in 40 mL methylene chloride and the resulting solution treated with 2.3 mL of 2-cyanoethyl-N,N,N',N'-tetraisopropylphosphorodiamidite and 600 mg of DIPA-tetrazole salt. After 15 hours at room temperature, the reaction was quenched by addition of 0.5 mL methanol. The reaction mixture was poured into 400 mL methylene chloride and the organic layer washed with 5% sodium bicarbonate solution (2×100 mL), and then dried over anhydrous sodium sulfate. Removal of solvents by rotary evaporation gave 5.8 g of crude product, which was purified by column chromatography over silica gel, eluted with $CH_2Cl_2$/methanol/TEA (100:2:1, v/v/v) to yield 3.6 g of pure Compound 1.

(b) Synthesis of Reagent compound 2 wherein $R^1$ is dimethoxytriphenyl (DMT), X is O, $X^1$—$X^2$—$X^3$ is cyclohexane —NH—CO$(CH_2)_5$NHCOCF$_3$, and $R^3$ is phosphoramidite.

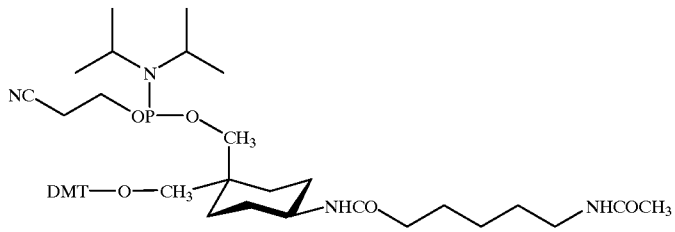

[COMPOUND 2]

Figure 3:
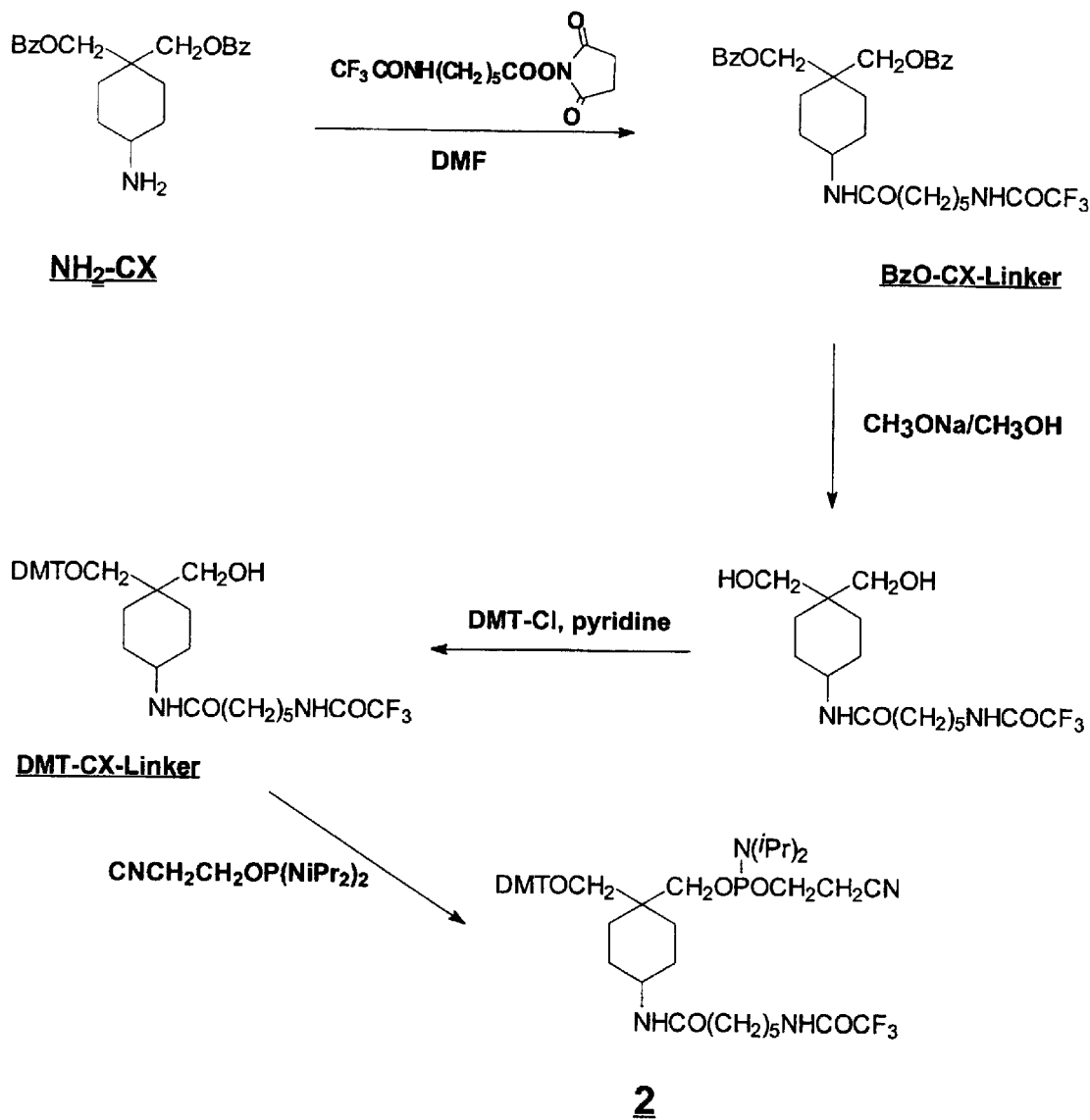
FIG. 3 is a schematic depiction of the synthetic protocol of Example 1(b)

The synthetic protocol for Compound 2 is outlined below and depicted in FIG. 3:

Step I: Synthesis of BzO-CX-Linker

To 15.0 g of the $NH_2$-CX intermediate (prepared in step 2 of Example 1a) dissolved in 150 mL methylene chloride, was added dropwise a solution of 21.2 g 6-trifluoroacetamido-caproic acid N-hydroxysuccinimde ester (Linker-NHSu) in 150 mL methylene chloride. The resulting mixture was stirred at room temperature for 15 min and then treated with 12.1 mL triethylamine. After 90 min stirring at room temperature, TLC analysis ($CH_2Cl_2$/ methanol, 9:1) indicated that the reaction had gone to completion.

Methylene chloride was removed by rotary evaporation, the resulting residue treated with 150 mL methanol, followed by 30 mL of 10% aqueous $Na_2CO_3$ Solution, and the mixture stirred for 1 hour at room temperature. After this time, the reaction mixture was poured into 1.0 L $CH_2Cl_2$ and the organic extract washed with 5% sodium bicarbonate solution. After drying over anhydrous sodium sulfate, the solvents were evaporated in vacuo to afford 22 g of crude product. Flash chromatographic purification using $CH_2Cl_2$/ methanol (100:3, v/v) as the eluent, afforded 10.6 g of pure product.

Step II: Synthesis of DMT-CX-Linker

To a stirred solution of 10.3 g BzO-CX-Linker in 100 mL DMF, was added 15 mL of 25% sodium methoxide in methanol, and the resulting mixture stirred at 0–5° C. for 1 hour. The pH of the solution was then adjusted to 7.0 by the addition of 45 g Dowex 50X8-100 resin to the reaction mixture followed by stirring for 15 min. The resin was filtered off and the filtrate evaporated to remove DMF. The resulting residue was dissolved in 5 mL methylene chloride and the product precipitated by the addition of 50 mL hexane. The product was then dried under high vacuum.

The crude product obtained in this manner was azeotroped twice with pyridine and then dissolved in 100 mL pyridine. To this was added 5.9 g of DMT-Cl and the reaction mixture stirred at room temperature, under argon, for 1.5 hours. The reaction was quenched by the addition of 3 mL methanol and stirred for 30 min. The reaction mixture was taken up in 500 mL methylene chloride, the organic extract washed with 5% $NaHCO_3$ solution (300 mL×2), and then dried over anhydrous sodium sulfate. Evaporation of the solvents in vacuo afforded 11.9 g of crude product, which was purified by column chromatography over silica gel, eluting with methylene chloride/methanol (100:2 v/v) to yield 5.7 g.

Step III: Synthesis of N-Linker-CX-CED Phosphoramidite

The intermediate obtained in step II above was converted to the corresponding phosphoramidite using standard methods. Thus, 3.0 g of DMT-CX-Linker was dissolved in 50 mL methylene chloride and the resulting solution treated with 2.2 mL of 2-cyanoethyl-N,N,N',N'-tetraisopropylphosphorodiamidite and 560 mg of DIPA-tetrazole salt. After 15 hours at room temperature, the reaction was quenched by addition of 1.0 mL methanol. The reaction mixture was poured into 300 mL methylene chloride, the organic layer washed with 5% sodium bicarbonate solution (2×80 mL), and then dried over anhydrous sodium sulfate. Removal of solvents by rotary evaporation gave 4.3 g of crude product, which was purified by column chromatography over silica gel, eluted with $CH_2Cl_2$/ methanol/TEA (100:1:1, v/v/v)—yield 3.1 g of pure Compound 2.

(c) Synthesis of Reagent compound 3 wherein $R^1$ is dimethoxytriphenyl (DMT), X is O, $X^1$—$X^2$—$X^3$ is cyclohexane —NH—CO—fluorescein, and $R^3$ is phosphoramidite.

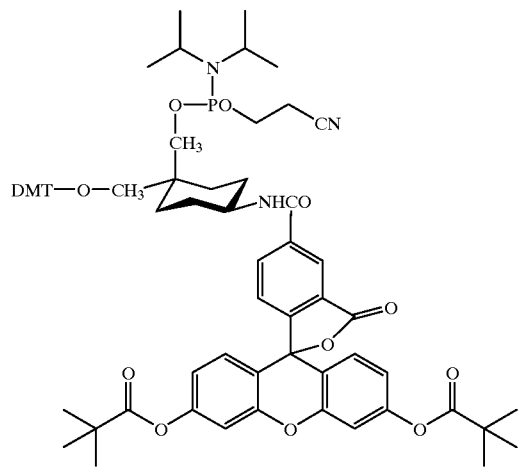

[COMPOUND 3]

Figure 4:
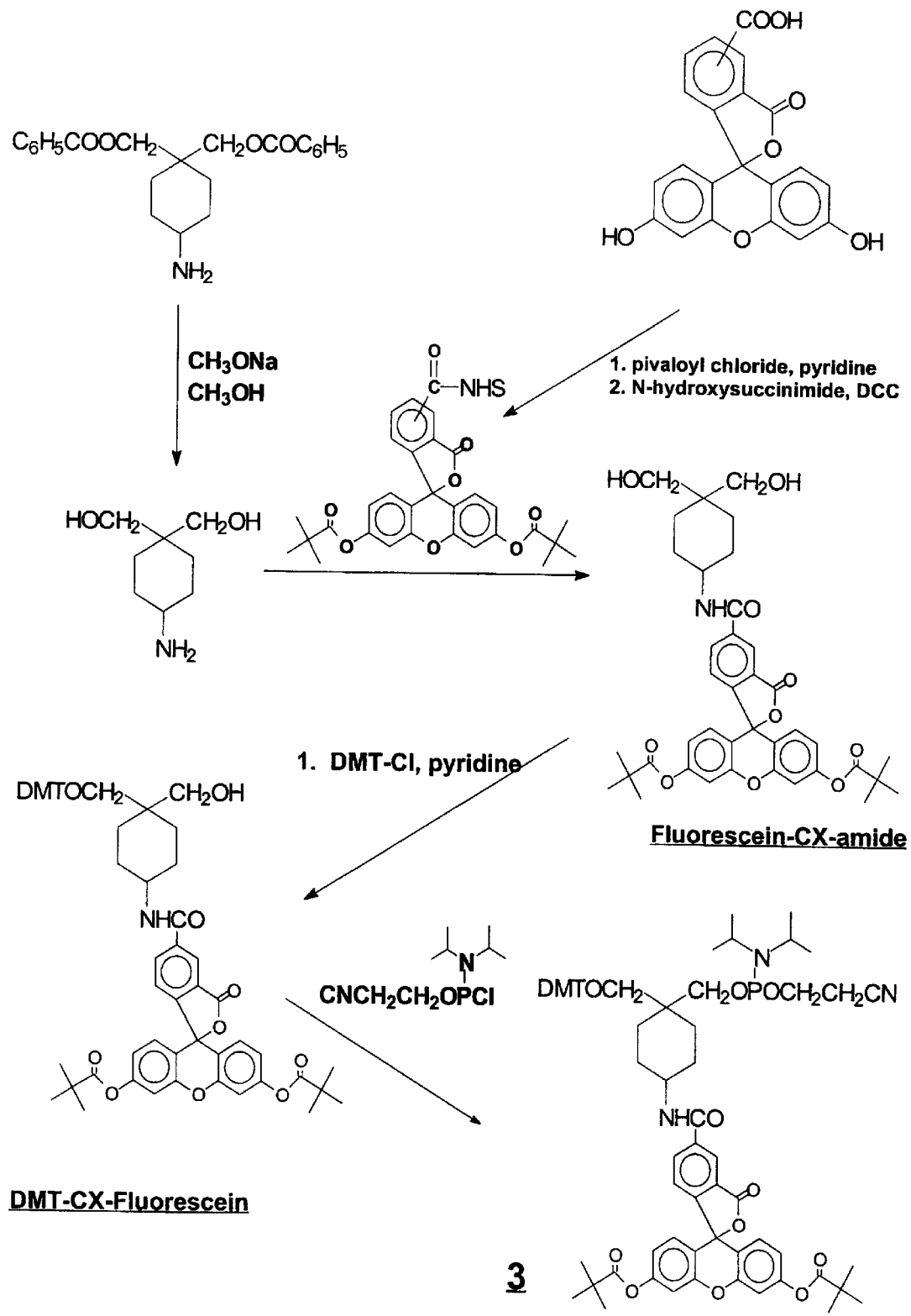
FIG. 4 is a schematic depiction of the synthetic protocol of Example 1(c)

The synthetic protocol for Compound 3 is outlined below and depicted in FIG. 4:

Step I: Synthesis of 4-amino-1,1-bis(hydroxymethyl) cyclohexane

To 30.6 g of $NH_2$-CX dissolved in 400 mL of methanol was added 39.3 mL of a solution of sodium methoxide (25% w/v) in methanol. The reaction mixture was stirred at ambient temperature for 1 hour under anhydrous conditions. The reaction was monitored by TLC using a mixture of methylene chloride:methanol (9:1) as solvent. Solvents were removed by rotary evaporation and the residue treated with 60 mL water, cooled in an ice bath, and then neutralied by the slow addition of hydrochloric acid. The reaction mixture was extracted with methylene chloride (4×100 mL), and the aqueous portion concentrated in vacuo to give 21.5 g of product containing sodium chloride. The residue was treated with 200 mL methanol, filtered, and solvents removed in vacuo to give 13.2 g of the desired product.

Step II: 5-(& 6-) Carboxy Fluorescein Dipivaloate

To a solution of 25 g 5-(&- 6)-carboxy fluorescein in 200 mL pyridine, was added 25.8 g of diisopropylethyl amine and the resulting mixture cooled to −10° C. To the cooled solution was added dropwise 32.8 mL of pivaloyl chloride, and the mixture stirred for 2 hours under argon. The reaction mixture was allowed to warm up to room temperature over 2 hours. The reaction mixture was evaporated to dryness, and the residue extracted with 1.0 L methylene chloride. The organic extract was washed with water (2×500 mL), dried over anhydrous sodium sulfate, filtered, and concentrated in vacuo to afford 43.4 g of crude product. Flash chromatographic purification of this crude product (silica gel, $CH_2Cl_2$/MeOH, gradient elution 2–8% MeOH) afforded 22.0 g of pure product.

Step III: 5-(& 6-)Carboxyfluorescein Dipivaloyl Succinimidyl Ester

To a solution of 28.3 g 5-(and 6-) carboxyfluorescein dipivaloate in 250 mL methylene chloride, under argon, was added 7.1 g N-hydroxysuccinimide followed by 13 g of DCC. The reaction mixture was stirred at ambient temperature overnight under anhydrous conditions. The reaction mixture was filtered and the filtrate evaporated to dryness to give 39 g of crude product. This product was purified by column chromatography over silica gel, using ethyl acetate/hexane (1:1, v/v) as the eluent to yield 27.4 g.

Step IV: Fluorescein-CX-amide 13.2 g of 4-amino-1,1-bis(hydroxymethyl)cyclohexane was azeotroped with 50 mL of anhydrous DMF using rotary evaporation at 55° C. To this was added 75 mL anhydrous DMF followed by 19.5 g of 5-(& 6-)carboxyfluorescein dipivaloyl succinimidyl ester under argon. 3.3 g of triethylamine was added and the reaction mixture stirred at room temperature overnight under anhydrous conditions. The solution was evaporated to dryness using rotary evaporation at 55±5° C. The residue was extracted into 500 mL methylene chloride and the organic extract washed with water (2×100 mL). After drying over anhydrous sodium sulfate, solvents were removed in vacuo to afford 32 g of crude product. Flash chromatographic purification of this crude product (silica gel, $CH_2Cl_2$/MeOH, gradient elution 3–6% MeOH) afforded 7.4 g of pure product.

Step V: Synthesis of DMT-CX-Fluorescein

To 7.4 g of product obtained from step IV above, was added 50 mL of anhydrous pyridine and the mixture azeotroped. The residue was dissolved in 50 mL anhydrous pyridine. To this was added 4.6 g of DMT-Cl and the reaction mixture stirred at room temperature overnight, under argon. The reaction was quenched by the addition of 10 mL methanol and stirred for 30 min.

The reaction mixture was taken up in 250 mL methylene chloride, the organic extract washed with 75 mL of a 5% $NaHCO_3$ solution, and then dried over anhydrous sodium sulfate. Evaporation of the solvents in vacuo afforded 13.5 g of crude product, which was purified by column chromatography over silica gel, eluting first with 1.0 L hexane:ethyl acetate (6.5:3.5, v/v) & then with 2.0 L hexane:ethyl acetate (1:1, v/v) to yield 5.8 g.

Step VI: Synthesis of Fluorescein-CX-CED Phosphoramidite

The intermediate obtained in step V above was converted to the corresponding phosphoramidite using standard methods. Thus, 5.8 g of DMT-CX-Fluorescein was dissolved in 100 mL anhydrous methylene chloride and the resulting solution treated with 3.0 g of diisopropylethylamine, followed by 1.9 g of 2-cyanoethyl N,N-diisopropylchlorophosphoroamidite. After 2 hours at room temperature, the reaction was quenched by addition of 1.0 mL methanol. The reaction mixture was poured into 200 mL methylene chloride, the organic layer washed with 5% sodium bicarbonate solution (2×75 mL), and then dried over anhydrous sodium sulfate. Removal of solvents by rotary evaporation gave 8.0 g of crude product, which was purified by column chromatography over silica gel, eluted with hexane/ethyl acetate/TEA (gradient elution—30.0 to 35.0% ethyl acetate in hexane containing 0.5% TEA) to yield 4.2 g of pure Compound 3.

(d) Synthesis of Reagent compound 4 wherein $R^1$ is dimethoxytriphenyl (DMT), X is O, $X^1$—$X^2$—$X^3$ is cyclohexane —NH—CO($CH_2$)$_5$NHCO$CF_3$, and $R^3$ is —OCOCH$_2$CH$_2$CONH—CPG.

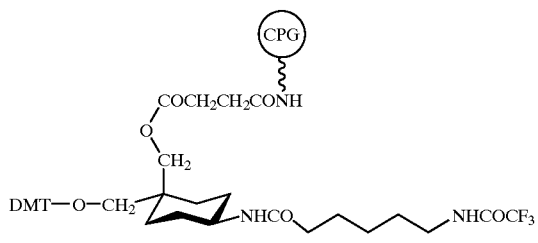

[COMPOUND 4]

The synthetic protocol for Compound 4 is outlined below:

Step 1: Preparation of N-Linker succinate:

To a stirred solution of 1.95 g of DMT-N-Linker-CX in 20 mL anhydrous methylene chloride, was added 100 mg of 4-dimethylaminopyridine followed by 1.2 g of succinic anhydride. The resulting solution was stirred at room temperature for 15 hours. The reaction mixture was quenched by the addition of 10 mL of a 5% solution of sodium bicarbonate in water and the mixture stirred for 30 min. The crude reaction mixture was then evaporated to dryness in vacuo and the resulting residue extracted twice with 50 mL of methylene chloride.

The organic extract was washed with 5% aqueous citric acid solution (2×20 mL) and then dried over anhydrous sodium sulfate. Evaporation of the solvents in vacuo afforded 1.9 g of the crude product. This product was purified by flash chromatography over silica gel using $CH_2Cl_2$/$CH_3OH$ (100:5, v/v) as the eluant.

Step 2: Preparation of N-Linker-CPG:

To a suspension of 4.0 g of LCAA-CPG in 14 mL of methylene chloride in a 50 mL round bottomed flask, was added 105 mg of N-Linker succinate and 0.7 mL of triethylamine. This was followed by the addition of 20 mg of anhydrous hydroxybenzotriazole and 70 mg of benzotrizolyl-N-oxy-tris(dimethylamino) phosphonium hexafluorophosphate (BOP reagent).

The resulting mixture was gently shaken for 2 hours, then filtered, washed with methylene chloride (10 mL×2), and air dried. The solid was transferred to a 100 mL round bottom flask, treated with 36 mL pyridine, 4 mL of acetic anhydride and 0.4 mL of N-methylimidazole, and the resulting suspension shaken overnight. The mixture was then suction filtered, and the solid washed with methanol (10 mL×3). The solid was washed further with methylene chloride (10 mL×3), followed by anhydrous ether (10 mL×3). The solid was air dried and then finally dried overnight under high vacuum.

(e) Synthesis of Reagent compound 5 wherein $R^1$ is dimethoxytriphenyl (DMT), X is O, $X^1$—$X^2$—$X^3$ is cyclohexane —NH—CO—biotin, and $R^3$ is —OCOCH$_2$CH$_2$CONH—CPG.

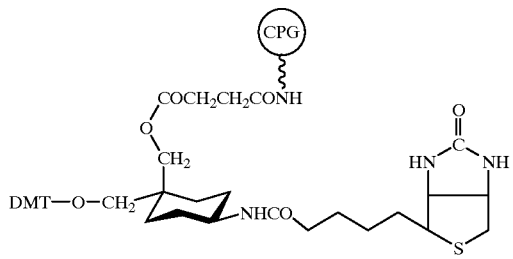

[COMPOUND 5]

Figure 5:
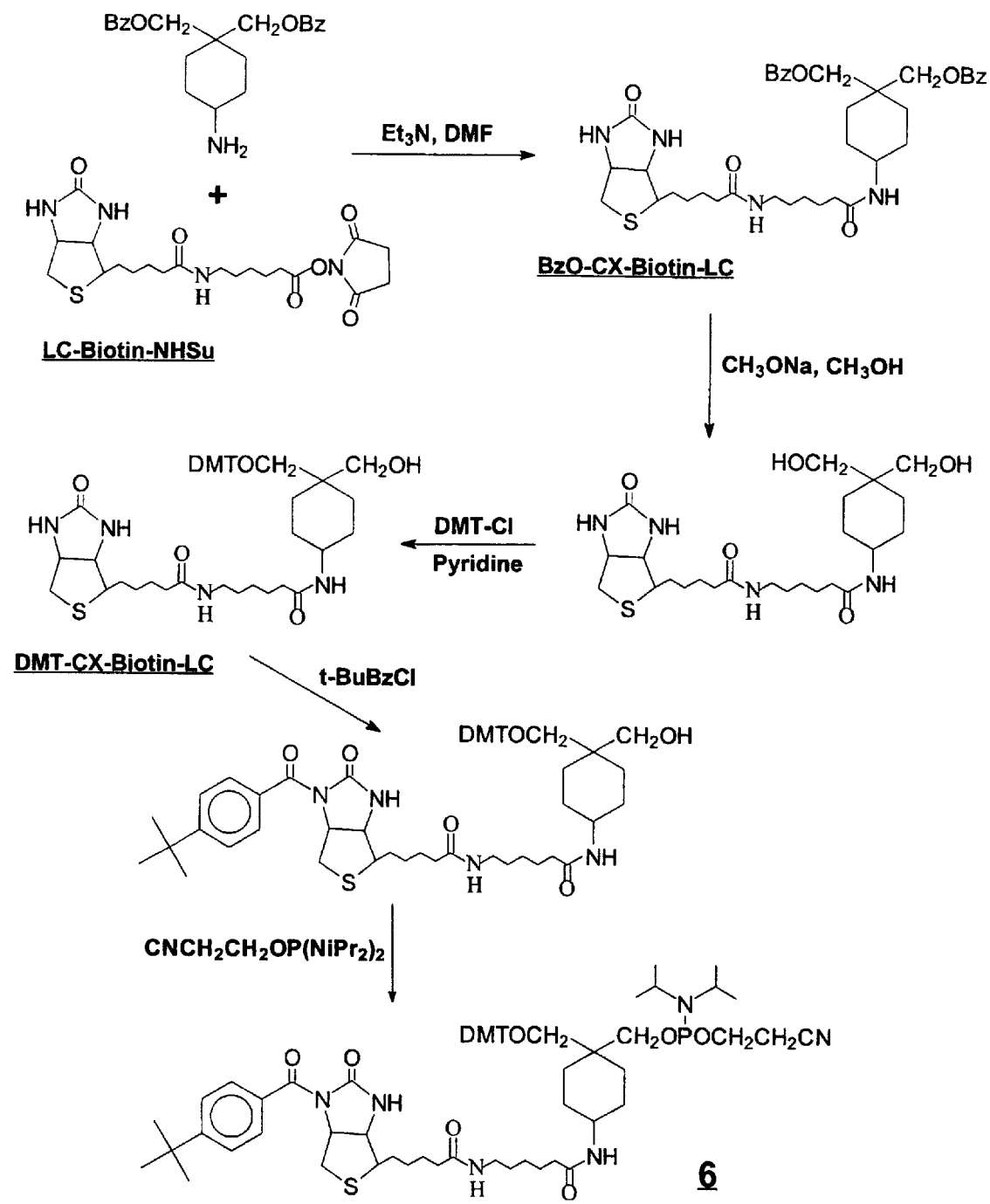
FIG. 5 is a schematic depiction of the synthetic protocol of Example 1(f).

The synthetic protocol for Compound 5 is illustrated in FIG. 5, and outlined below:

Step 1: Preparation of Biotin succinate:

To a stirred solution of 2.0 g of DMT-CX-Biotin in 20 mL anhydrous methylene chloride, was added 100 mg of 4-dimethylaminopyridine followed by 1.2 g of succinic anhydride. The resulting solution was stirred at room temperature for 15 hours at which point TLC analysis of the reaction mixture (9:1 CH$_2$CL$_2$/CH$_3$OH) indicated that the reaction was complete.

The reaction mixture was quenched by the addition of 10 mL of a 5% solution of sodium bicarbonate in water and the mixture stirred for 30 min. The crude reaction mixture was then evaporated to dryness in vacuo and the resulting residue extracted twice with 50 mL of methylene chloride. The organic extract was washed with 5% aqueous citric acid solution (20 mL×2) and then dried over anhydrous sodium sulfate. Evaporation of the solvents in vacuo afforded 2.4 g of the crude product. This product was purified by flash chromatography over silica gel using CH$_2$Cl$_2$/CH$_3$OH (100:4, v/v) as the eluant.

Step 2: Preparation of Biotin-CPG:

To a suspension of 4.0 g of LCAA-CPG in 14 mL of methylene chloride in a 50 mL round bottomed flask, was added 110 mg of Biotin succinate and 0.7 mL of triethylamine. This was followed by the addition of 20 mg of anhydrous hydroxybenzotriazole and 70mg of BOP reagent. The resulting mixture was gently shaken for 2 hours, then filtered, washed with methylene chloride (20 mL×2), and air dried. The solid was transferred to a 100 mL round bottom flask, treated with 36 mL pyridine, 4 mL of acetic anhydride and 0.4 mL of N-methylimidazole, and the resulting suspension shaken overnight.

The mixture was then suction filtered, and the solid washed with methanol (10 mL×3). The solid was washed further with methylene chloride (10 mL×3), followed by anhydrous ether (10 mL×3). The solid was air dried and then finally dried overnight under high vacuum. The loading of the biotin derivatized CPG was determined to be 31.3 μmole/gram using standard methods.

(f) Synthesis of Reagent compound 6 wherein $R^1$ is dimethoxytriphenyl (DMT), X is O, $X^1$—$X^2$—$X^3$ is cyclohexane —NH—CO(CH$_2$)$_5$NHCO—biotin, and $R^3$ is phosphoramidite.

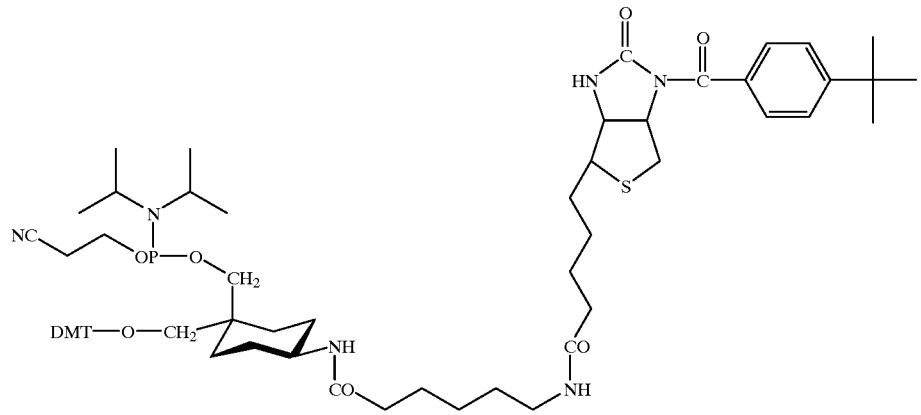

[COMPOUND 6]

The synthetic protocol for Compound 6 is outlined below and depicted in FIG. 5:

Step I: Synthesis of BzO-CX-Biotin-LC

To 32.0 g of the NH$_2$-CX intermediate (prepared as discussed in Example 1a) dissolved in 500 mL anhydrous methylene chloride, was added dropwise a solution of 39.5 g LC Biotin-NHSu (prepared by the reaction of 6-aminocaproic acid with the NHSu-ester of biotin) in 500 mL anhydrous DMF. The resulting mixture was stirred at room temperature for 15 min and then treated with 12.1 mL triethylamine. After 2 hours stirring at room temperature, TLC analysis (CH$_2$Cl$_2$/methanol, 9:1) indicated that the reaction had gone to completion. Methylene chloride was removed by rotary evaporation, the resulting solution treated with methanol (20 mL) followed by 10% aqueous Na$_2$CO$_3$ (20 mL), and the mixture stirred for 1 h at room temperature. After this time, the reaction mixture was poured into 2.0 L ethyl acetate and the organic extract washed with brine (500 mL×2). After drying over anhydrous sodium sulfate, the solvents were evaporated in vacuo to afford 64 g of crude product. Flash chromatographic purification of this crude product (silica gel, CH$_2$Cl$_2$/MeOH, gradient elution 5–8% MeOH) afforded 30 g of pure product.

Step II: Synthesis of DMT-CX-Biotin-LC

To a stirred solution of 29.8 g of BzO-CX-Biotin-LC in 300 mL DMF, was added 34.5 mL of 25% sodium methoxide in methanol, and the resulting mixture stirred at 0–5° C. for 1 hour. The pH of the solution was then adjusted to 7.0 by the addition of 100 g Dowex 50X8-100 resin to the reaction mixture followed by stirring for 15 min. The resin was filtered off and the filtrate evaporated to remove DMF. The resulting residue was dissolved in 60 mL methylene chloride and the product precipitated by the addition of 200 mL hexane. The product was then dried under high vacuum.

The crude product obtained in this manner was azeotroped twice with pyridine and then dissolved in 500 mL pyridine. To this was added 14.0 g of DMT-Cl and the reaction mixture stirred at room temperature, under argon, for 1.5 hours. The reaction was quenched by the addition of 5 mL methanol and stirred for 30 min. The reaction mixture was taken up in 1.5 L methylene chloride, the organic extract washed with 5% NaHCO$_3$ solution (500 mL×2), and then dried over anhydrous sodium sulfate. Evaporation of the solvents in vacuo afforded 26.0 g of crude product, which was purified by column chromatography over silica gel, eluting with methylene chloride/methanol (100:8 v/v) to yield 12.0 g.

Step III: Synthesis of tBuBz-DMT-CX-Biotin-LC

To a stirred solution of 12.0 g of DMT-CX-Biotin in 300 mL anhydrous pyridine, was added 13.0 mL TMSCl and the mixture stirred at room temperature for 2 hours, under argon. This was followed by the addition of 4.4 mL of 4-tert-butyl benzoyl chloride to the reaction mixture and the reaction was allowed to proceed at room temperature for 3 hours. The reaction was worked up by the addition of 80 mL water followed by stirring for 1 hour at room temperature. The reaction mixture was evaporated to remove most of the pyridine and the resulting residue dissolved in 1.0 L methylene chloride. The organic extract was washed with 5% NaHCO$_3$ solution (300 mL×2), and then dried over anhydrous sodium sulfate. Removal of solvents by rotary evaporation gave 18.3 g of crude product.

Flash chromatographic purification of this crude product (silica gel, EtOAc/CH$_2$Cl$_2$/MeOH, gradient elution with solutions containing 5–10 parts MeOH in EtOAc/CH$_2$Cl$_2$, 50:50 parts, v/v/v) afforded 8.3 g of pure product.

Step IV: Synthesis of LC-Biotin-CX-CED Phosphoramidite

The intermediate obtained in step III above was converted to the corresponding phosphoramidite using standard methods. Thus, 8.2 g of $^t$BuBz-DMT-CX-Biotin-LC was dissolved in 100 mL methylene chloride and the resulting solution treated with 4.0 mL of 2-cyanoethyl-N,N,N',N'-tetraisopropylphosphorodiamidite and 600 mg of DIPA-tetrazole salt. After 15 hours at room temperature, the reaction was quenched by addition of 0.5 mL methanol. The reaction mixture was poured into 1.0 L methylene chloride, the organic layer washed with 5% sodium bicarbonate solution (2×300 mL), and then dried over anhydrous sodium sulfate. Removal of solvents by rotary evaporation gave 10.5 g of crude product, which was purified by column chromatography over silica gel, and eluted with CH$_2$Cl$_2$/methanol/TEA (100:1:1, v/v/v) to yield 5.0 g of pure Compound 6.

EXAMPLE 2

Reagents in accordance with the present invention can be incorporated into oligomers comprising nucleotide and non-nucleotide units, by substituting the present non-nucleotide reagents in place of selected nucleotide units in standard nucleotide synthesis protocols, such as automated DNA/RNA synthesis protocols.

(a) Use of Biotin-CX by direct binding to polystyrene plates:

Synthetic oligomers, containing one or more biotin residues as part of the sequence, were labelled with a 5'-phosphate group. This 5'-phosphate moiety is then used to covalently bind the oligomer onto polystyrene microtiter plates.

The unbound probes are washed off and the bound probes are detected by the reaction of biotin with streptavidin conjugated to alkaline phosphatase. The alkaline phosphatase catalyses the hydrolysis of a chromogenic substrate.

Thus, 30 mers were synthesized which included a 5' phosphate moiety and biotin residue labels at positions 13, 19 and 25 (5'→3'). Two different oligomers were synthesized: one with Biotin-CX phosphoramidite prepared in accordance with Example 1 and the second oligomer with Biotin-dC (a commercially available nucleosidic biotin phosphoramidite).

Each of the oligomers was diluted to a concentration of 10 fmol/μL in distilled water. The oligomers were denatured by heating at 95° C. for 10 min. followed by cooling over ice for 10 min. The appropriate amount of denatured oligomers were added to the wells of cold Covalink NH modules, followed by the addition of EDC buffer containing Meim and then overnight incubation at 50° C. Unbound probes were washed off and the bound oligomers were detected by binding of streptavidin conjugated to alkaline phosphatase. pNPP was used as the substrate for the enzyme and the development of color was monitored at 405 nm. The above experiment was repeated using both oligomers at a concentration of 5 fmol/μL. The signal intensities obtained using the two different biotin structures were compared. At 5 fmol/μL, biotin-CX gave 95% of the reading (OD 405 nm) of biotin-dC. At 10 fmol/μL, biotin-CX gave 106% of the reading of biotin-dC.

(b) Use of Biotin-CX in a hybridization assay:

The oligomer Alu-011 is a 56 mer with one internal biotin residue at position 25 (5'→3'), designed to be complementary to the template Alu-011A. Two different oligomers were synthesized: One with Biotin-CX and the other with Biotin-dC. Oligomers were synthesized in the Trityl-ON mode and then cartridge purified using PolyPak (Glen Research Inc.) reverse phase cartridges. These two oligomers were used in hybridization assays to detect the template Alu-011A.

The template Alu-011A was bound to CovaLink polystyrene microtiter plates using the 5'-phosphate group as described above. The probes were diluted to 25 fmol/μL in hybridization buffer and 100 μL of the diluted probes was added to the wells and incubated at 42° C. for from 5 hours to overnight. Excess probes were washed off with buffer and the bound biotin-labelled probes were detected as described above.

The signal intensities obtained using the two different biotin structures were compared. Under identical conditions, Biotin-CX labelled oligomers generated approximately a 5-fold stronger signal than oligomers labelled with Biotin-dC.

All publications and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A non-nucleotide reagent which is capable of substituting for a nucleotide unit in an oligonucleotide, said reagent comprising a compound of the formula:

$$R^1-X-CH_2-\underset{\underset{\underset{X^3}{|}}{\underset{X^2}{|}}}{\overset{\overset{X^1}{\|}}{C}}-CH_2-R^3$$

wherein
- $R^1$ is selected from the group consisting of hydrogen, acid-sensitive, base-stable blocking groups and acyl capping groups;
- X is O;
- $X^1$ is a substituted or unsubstituted $C_5$ to $C_7$ cyclic moiety incorporating the carbon atom of the formula;
- $X^2$ is selected from the group consisting of O, S, $CH_2$, NH and N=N; and
- $X^3$ is hydrogen, or a linking functional group which is capable of linking with a functional moiety; and
- $R^3$ is a phosphorus linking group of the formula $$-O\underset{\underset{X^5}{|}}{\overset{\overset{X^4}{|}}{P}} \quad \text{or} \quad -O\underset{\underset{X^7}{|}}{\overset{\overset{X^6}{|}}{P}}=O$$
(a) (b)

wherein
- $X^4$ is halogen or substituted amino,
- $X^5$ is alkyl, alkoxy or phenoxy, or a cyano derivative thereof,
- $X^6$ is halogen, amino or O, and
- $X^7$ is allyl, aryloxy, or $X^7$ can be H only if $X^6$ is O, or $R^3$ can be absent so that the reagent is bonded, either directly or through an intermediate group, to a solid support.

2. A reagent as recited in claim 1, wherein $R^1$ is selected from the group consisting of triphenylmethyl compounds and alkoxy derivatives thereof.

3. A reagent as recited in claim 2, wherein $R^1$ is dimethoxytriphenyl.

4. A reagent as recited in claim 1, wherein $X^1$ is cyclohexane.

5. A reagent as recited in claim 1, wherein $X^2$ is NH.

6. A reagent as recited in claim 1, wherein $X^3$ is a linking group of the formula $$-CO-(CH_2)_n-NH-$$

wherein n is an integer from 0 to 20.

7. A reagent as recited in claim 1, wherein $X^3$ further comprises a functional moiety.

8. A reagent as recited in claim 7, wherein the functional moiety is selected from the group consisting of labels, metal chelators and specific binding agents.

9. A reagent as recited in claim 8, wherein the functional moiety is a fluorescent label.

10. A reagent as recited in claim 9, wherein the fluorescent label is fluorescein.

11. A reagent as recited in claim 8, wherein the functional moiety is a specific binding agent.

12. A reagent as recited in claim 11, wherein the specific binding agent is biotin.

13. A reagent as recited in claim 1, wherein $R^3$ is selected from the group consisting of phosphodiesters, phosphotriesters, phosphites, phosphoramidites, H-phosphonates, alkyl-phosphonates, and phosphorothioates.

14. A reagent as recited in claim 1, wherein $R^3$ comprises a bond, either directly or through an intermediate group, to a solid support.

15. A reagent as recited in claim 14, wherein the intermediate group comprises $-O-CO(CH_2)_2-CO-$.

16. An oligomer having both nucleotide and non-nucleotide units, at least one of said non-nucleotide units comprising a compound of the formula:

$$R^1-X-CH_2-\underset{\underset{\underset{X^3}{|}}{\underset{X^2}{|}}}{\overset{\overset{X^1}{\|}}{C}}-CH_2-R^3$$

wherein
- $R^1$ is selected from the group consisting of hydrogen, acid-sensitive, base-stable blocking groups and acyl capping groups, or $R^1$ is a bond to an adjacent monomeric unit;
- X is O;
- $X^1$ is a substituted or unsubstituted $C_5$ to $C_7$ cyclic moiety incorporating the carbon atom of the formula;
- $X^2$ is selected from the group consisting of O, S, $CH_2$, NH and N=N; and
- $X^3$ is hydrogen, or a linking functional group which is capable of linking with a functional moiety; and
- $R^3$ is a phosphorus linking group of the formula $$-O\underset{\underset{X^5}{|}}{\overset{\overset{X^4}{|}}{P}} \quad \text{or} \quad -O\underset{\underset{X^7}{|}}{\overset{\overset{X^6}{|}}{P}}=O$$
(a) (b)

wherein
- $X^4$ is halogen or substituted amino,
- $X^5$ is alkyl, alkoxy or phenoxy, or a cyano derivative thereof,
- $X^6$ is halogen, amino or O, and
- $X^7$ is alkyl, alkoxy, aryloxy, or $X^7$ can be H only if $X^6$ is O, or $R^3$ is a bond to an adjacent monomeric unit or directly or through an intermediate group a solid support, with the proviso that at least one of $R^1$ and $R^3$ is a bond.

17. A method for preparing an oligomer having both nucleotide and non-nucleotide units, comprising coupling at least one non-nucleotide unit comprising a compound of the formula:

$$R^1-X-CH_2-\underset{\underset{\underset{X^3}{|}}{\underset{X^2}{|}}}{\overset{\overset{X^1}{\|}}{C}}-CH_2-R^3$$

wherein $R^1$ is selected from the group consisting of hydrogen, acid-sensitive, base-stable blocking groups and acyl capping groups, or $R^1$ is a bond to an adjacent monomeric unit;

X is O;

$X^1$ is a substituted or unsubstituted $C_5$ to $C_7$ cyclic moiety incorporating the carbon atom of the formula;

$X^2$ is selected from the group consisting of O, S, $CH_2$, NH and N=N; and $X^3$ is hydrogen, or a linking functional group which is capable of linking with a functional moiety; and $R^3$ is a phosphorus linking group of the formula $$-\underset{\underset{X^5}{|}}{\overset{\overset{X^4}{|}}{OP}} \quad \text{or} \quad -\underset{\underset{X^7}{|}}{\overset{\overset{X^6}{|}}{OP}}=O$$
(a)        (b)

wherein $X^4$ is halogen or substituted amino, $X^5$ is alkyl, alkoxy or phenoxy, or a cyano derivative thereof, $X^6$ is halogen, amino or O, and $X^7$ is alkyl, alkoxy aryloxy, or $X^7$ can be H only if $X^6$ is O, or $R^3$ can be absent so that the reagent is bonded, either directly or through an intermediate group, to an adjacent monomeric unit or a solid support to at least one nucleotide monomeric unit by a bond at either $R^1$ or $R^3$.

18. A kit for preparing an oligomer having both nucleotide and non-nucleotide units, comprising a receptacle adapted to hold one or more individual reagent containers; and a first container containing a reagent in accordance with the formula:

$$R^1-X-CH_2-\underset{\underset{\underset{X^3}{|}}{\underset{X^2}{|}}}{\overset{\overset{X^1}{\|}}{C}}-CH_2-R^3$$

wherein $R^1$ is selected from the group consisting of hydrogen, acid-sensitive, base-stable blocking groups and acyl capping groups;

X is O;

$X^1$ is a substituted or unsubstituted $C_5$ to $C_7$ cyclic moiety incorporating the carbon atom of the formula;

$X^2$ is selected from the group consisting of O, S, $CH_2$, NH and N=N; and $X^3$ is hydrogen, or a linking functional group which is capable of linking with a functional moiety; and $R^3$ is a phosphorus lining group of the formula $$-\underset{\underset{X^5}{|}}{\overset{\overset{X^4}{|}}{OP}} \quad \text{or} \quad -\underset{\underset{X^7}{|}}{\overset{\overset{X^6}{|}}{OP}}=O$$
(a)        (b)

wherein $X^4$ is halogen or substituted amino, $X^5$ is allyl, alkoxy or phenoxy, or a cyano derivative thereof, $X^6$ is halogen, amino or O, and $X^7$ is alkyl, alkoxy $R^3$ can be absent so that the reagent is bonded, either directly or through an intermediate group, to a solid support.

19. A kit as recited in claim 18, further comprising a second container containing (1) a reagent used in the synthesis of oligomers, or (2) a reagent used in the detection of a functional moiety associated with said reagent.

20. A chemical intermediate for synthesizing a non-nucleotide reagent which is capable of forming a oligomer with nucleotide units, said intermediate comprising a compound of the formula:

$$R^1-X-CH_2-\underset{\underset{\underset{X^3}{|}}{\underset{X^2}{|}}}{\overset{\overset{X^1}{\|}}{C}}-CH_2-R^3$$

wherein $R^1$ is hydrogen;

X is oxygen;

$X^1$ is cyclohexane, $X^2$ is NH, and $X^3$ is H; and $R^3$ is OH.

* * * * *